United States Patent
Rousseau

(10) Patent No.: US 9,533,446 B2
(45) Date of Patent: Jan. 3, 2017

(54) SUTURE HAVING A RESTRAINING ELEMENT AT AN END AND METHOD AND USE THEREOF

(71) Applicant: Ethicon LLC, San Lorenzo, PR (US)

(72) Inventor: Robert A. Rousseau, Ottsville, PA (US)

(73) Assignee: Ethicon, Inc., Somerville, NJ (US)

(*) Notice: Subject to any disclaimer, the term of this patent is extended or adjusted under 35 U.S.C. 154(b) by 0 days.

(21) Appl. No.: 14/967,814

(22) Filed: Dec. 14, 2015

(65) Prior Publication Data

US 2016/0106411 A1 Apr. 21, 2016

Related U.S. Application Data

(63) Continuation-in-part of application No. 14/887,496, filed on Oct. 20, 2015.

(60) Provisional application No. 62/066,597, filed on Oct. 21, 2014.

(51) Int. Cl.
| | |
|---|---|
| *B32B 37/00* | (2006.01) |
| *B29C 65/08* | (2006.01) |
| *A61B 17/06* | (2006.01) |
| *B29L 31/00* | (2006.01) |
| *A61B 17/00* | (2006.01) |

(52) U.S. Cl.
CPC ......... *B29C 65/08* (2013.01); *A61B 17/06166* (2013.01); *A61B 2017/00526* (2013.01); *A61B 2017/06176* (2013.01); *B29L 2031/753* (2013.01)

(58) Field of Classification Search
CPC ............... B29C 65/08; A61B 17/06166; A61B 2017/0619

USPC ............... 156/73.1, 580.1, 580.2
See application file for complete search history.

(56) References Cited

U.S. PATENT DOCUMENTS

| | | | |
|---|---|---|---|
| 5,964,765 A | 10/1999 | Fenton, Jr. et al. | |
| 6,010,525 A * | 1/2000 | Bonutti | A61B 17/0487 606/148 |
| 6,159,234 A * | 12/2000 | Bonutti | A61B 17/0487 606/148 |
| 6,848,152 B2 | 2/2005 | Genova et al. | |
| 8,100,940 B2 | 1/2012 | Leung et al. | |
| 8,297,330 B2 | 10/2012 | O'Neill | |
| 8,323,316 B2 | 12/2012 | Maiorino et al. | |
| 8,333,788 B2 | 12/2012 | Maiorino | |
| 8,403,017 B2 | 3/2013 | Maiorino et al. | |
| 9,023,081 B2 | 5/2015 | Maiorino et al. | |
| 9,038,688 B2 | 5/2015 | Maiorino et al. | |
| 2003/0149447 A1 | 8/2003 | Morency et al. | |
| 2005/0216059 A1* | 9/2005 | Bonutti | A61B 17/0487 606/232 |
| 2005/0267531 A1 | 12/2005 | Ruff et al. | |
| 2006/0116718 A1 | 6/2006 | Leiboff | |
| 2009/0248067 A1 | 10/2009 | Maiorino | |
| 2014/0025111 A1* | 1/2014 | Bonutti | A61B 17/0401 606/232 |

FOREIGN PATENT DOCUMENTS

| | | |
|---|---|---|
| WO | WO 2012/004758 | 1/2012 |
| WO | WO 2015/069042 | 5/2015 |

* cited by examiner

Primary Examiner — James Sells

(57) ABSTRACT

Polymeric fibers, and apparatuses for and methods of processing such fibers to be useful as sutures, where at least one end of a fiber includes a termination feature. The termination feature is formed through the application of energy to a coiled region of the fiber.

21 Claims, 12 Drawing Sheets

SUTURE HAVING A RESTRAINING ELEMENT AT AN END AND METHOD AND USE THEREOF

CROSS-REFERENCE TO RELATED APPLICATIONS

This invention is a continuation-in-part of U.S. patent application Ser. No. 14/887,496, filed Oct. 20, 2015, which claims priority to U.S. Provisional Application No. 62/066,597, filed Oct. 21, 2014, the contents of each of which are incorporated herein by reference in their entireties.

FIELD

This invention relates, in general, to the method of producing features on polymer fibers, more particularly on a non-needled end of a surgical suture device through the application of energy, radiofrequency, heat, or ultrasonic energy. More particularly, the suture devices are self-retaining suture devices. The invention further relates to such devices and methods of using the devices.

BACKGROUND

Various surgical methods employing sutures have been used in the past for closing or binding together wounds in human or animal tissue, such as skin, muscles, tendons, internal organs, nerves, blood vessels, and the like. More specifically, the surgeon may use a surgical needle with an attached conventional suture (which can be a smooth monofilament or can be a multi-filament) to pierce the tissue alternately on opposing faces of the wound and thus sew the wound closed. Whether the wound is accidental or surgical, loop stitching is the method often used, especially for surface wounds. The surgical needle is then removed and the ends of the suture are tied, typically with at least three overhand throws to form a knot.

Since the time of their conception, self-retaining sutures (sometimes referred to as barbed sutures), which are generally of the same materials as conventional sutures, have offered numerous advantages over closing wounds with conventional sutures. A self-retaining suture includes an elongated body that has one or more spaced retainers, which project from the body surface along the body length. The retainers are arranged to allow passage of the self-retaining suture in one direction through tissue but resist movement of the self-retaining suture in the opposite direction. Thus, the main advantage of self-retaining sutures has been the provision of a non-slip attribute. Accordingly, self-retaining sutures do not have to be knotted at the completion of the stitch, the requirement for a surgical follower to maintain tension on a continuous stitch, as is done in the application of conventional sutures, is also eliminated. However, like a conventional suture, a self-retaining suture may be inserted into tissue using a surgical needle.

While the retainers provide the strength necessary to prevent the fiber from slipping backwards and eliminates the need for tying a knot at the termination point of the stitch, the initial placement of the stitch may require the use of some means to anchor the suture in the local tissue. In response to this need, stitch initiation features have been incorporated into some self-retaining devices. Stitches may be initiated through the creation of a typical surgeon's knot or through the addition of clips or other mechanical clamping devices appended to the suture. Stitches may be initiated through the use of integral looped ends, tabs, buttons and reverse retainer elements. However, many of these anchoring means suffer from defects or are burdensome or costly to prepare, and thus the present invention seeks to provide an improved anchoring means.

For example, U.S. Patent Publication No. 2005/0267531 discloses a barbed suture device that is produced with a variety of anchoring elements attached to the non-needled end of the device. However, preparing these anchoring elements requires multiple secondary operations with great precision in the production of the anchors and the subsequent attachment to the fiber. This increased demand for secondary operations increases the cost to produce the device. U.S. Patent Publication No. 2009/0248067 discloses an anchoring device with a looped end with barbed type projections, while U.S. Pat. No. 8,403,017 similarly discloses a suture having a looped end.

U.S. Patent Publication No. 2006/0116718 discloses a prosthetic screen tacking device that is produced with a perpendicular foot at one end, while U.S. Pat. No. 5,964,765 discloses a single-piece soft tissue fixation device that includes an elongated element terminating in a tip at one end and a receptacle at the other end which can be bonded with each other in a welded joint. The device is made of a heat-bondable, biocompatible material that can be ultrasonically or thermally welded. The tip and receptacle of the device can be textured or contoured or otherwise complementarily configured to promote mutual engagement prior to and during bonding. It should be noted, that the receptacle component is not intended to provide the stitch initiation functionality, but rather to provide a replacement for a knot with a welded joint of the looped suture. Producing these geometries, however, is difficult.

U.S. Patent Publication No. 2003/0149447 discloses a barbed suture device that is produced with a stopper on the non-needled end. It is proposed that the device can be produced through injection molding, cutting ribbon or stamping ribbon stock to produce the desired shapes. These methods, including the use of injection molding, however, limits options of materials given the required melt viscosity, and through any of these methods, may ultimately result in weaker sutures. U.S. Pat. No. 8,297,330 discloses a welded end effector, in which a knot is first tied in the suture, and subsequent fusing the knot to form a stopper. This method is inefficient since it requires the initial formation of a knotted structure, and then the application of energy may result in notches or dents due to the inherently open initial knotted structure. Similarly, U.S. Pat. Nos. 8,323,316 and 8,333,788 each disclose the use of a knotted end effector, where the end effector includes a knot including a plurality of throws. The initial formation of a knotted structure is to be avoided through the present invention.

PCT Publication No. WO 2012/004758 discloses a suture thread that is produced with a stopper on the non-needled end of the fiber. It is proposed that the stopper may be molded or heated and the free end of the suture fiber is inserted into the molten polymer to seal the fiber to the stopper. This method of production requires the addition of the secondary component to the base fiber in a molten condition and the thermal exposure to the molten polymer may result in a loss of strength in the base fiber due to elevated temperature exposure.

While the aforementioned publications have attempted to improve sutures by preparing end effectors, each of the attempts have been either ineffective, inefficient, or pose processing problems. There remains a need to produce a stitch initiation feature that does not require significant secondary processing steps, such as the formation of a knot, or the addition of secondary components, such as addition of molten material, and which results in a strong anchor to hold the suture in place.

SUMMARY

The present invention provides sutures, methods of making sutures, apparatuses for making sutures, and methods of using sutures, the sutures including a termination feature at its distal or trailing end. The invention may provide a suture having a first end and second end and a length therebetween, with a termination feature at the second end, and may include a plurality of retainers formed on the surface of the length of suture. The termination feature includes a coiled portion of a suture that has been subjected to exertion of energy to weld the coil into a stable anchor for the suture.

The suture may be formed by various methods, including one method of forming a suture including the steps of providing a length of suture material, the suture having a first end and second end and a length therebetween, and the suture including a plurality of retainers formed on the surface of the length of suture; winding the second end about a winding pin to form a coil, such that the coil does not become entangled; and subjecting the coiled second end to application of energy, the energy being sufficient to melt at least a portion of the coiled second end and form a solid unitary termination feature.

The method may include a method of continuously forming at least two sutures, each suture having a termination feature at a distal end and formed from a continuous line or strand of suture material. This method may include the steps of: providing a suture fiber having a first end and a second end, and an axial length suitable to form a termination feature-containing suture, the suture fiber being contained in such a fashion that the first end of the suture may be pulled though a winding pin without damage to the suture fiber; inserting the first end of the suture through a first end of a winding pin and out the second end of the winding pin, where the winding pin is disposed within an open interior of a welding die; gripping the first end of the suture with a gripping element, and pulling the first end of the suture in approximately a 90 degree angle with regard to the central axis of the winding pin; causing the suture to be wound about the outside of the winding pin so as to create a coil of suture; moving a welding horn into contact with the coil of suture; applying energy to the coil of suture so as to deform the coil of suture; allowing the deformed coil of suture to solidify to form a termination feature; and may additionally include the step of severing the suture at a location between the termination feature and the second end of the suture.

An apparatus may be included, which is used for forming a suture having a termination feature. The apparatus may include, among other components, a welding horn having a welding tip; a welding die having an open interior sized to be similar to the welding tip; and a winding pin disposed within the open interior of the welding die, the winding pin having a first end and second end and an open axial center connecting the first end and second end. The apparatus may further include a gripping element for grasping the suture material and pulling it to a desired length during the formation process.

Another aspect of the invention includes a method of forming a suture including the steps of: winding a second end of a suture material having a first end and a second end and a length therebetween about a winding pin to form a coil, such that the coil does not become entangled, where the winding pin includes: a first cylindrical component having a central axis defining an open interior, the open interior being defined by a side wall and terminating in an open end, the first cylindrical component having a slot extending through the side wall extending from the open end to a termination point axially offset from the open end; and a second cylindrical component having a central axis defining an at least partially open interior, the open interior being defined by a side wall and terminating in an open end, the second cylindrical component having a slot extending through the side wall extending from the open end to a termination point axially offset from the open end; the first and second cylindrical components being in concentric configuration with each other, where the first and second cylindrical components may be independently rotated with respect to each other; subjecting the coiled second end to application of energy, the energy being sufficient to melt at least a portion of the coiled second end and form a solid unitary termination feature.

In other aspects of the invention, there is an apparatus for forming a suture having a termination feature including: a welding horn having a welding tip; a welding die having an open interior sized to be similar to the welding tip; a winding pin, where the winding pin includes: a first cylindrical component having a central axis defining an open interior, the open interior being defined by a side wall and terminating in an open end, the first cylindrical component having a slot extending through the side wall extending from the open end to a termination point axially offset from the open end; and a second cylindrical component having a central axis defining an at least partially open interior, the open interior being defined by a side wall and terminating in an open end, the second cylindrical component having a slot extending through the side wall extending from the open end to a termination point axially offset from the open end; the first and second cylindrical components being in concentric configuration with each other, where the first and second cylindrical components may be independently rotated with respect to each other.

DETAILED DESCRIPTION

Figure 1:
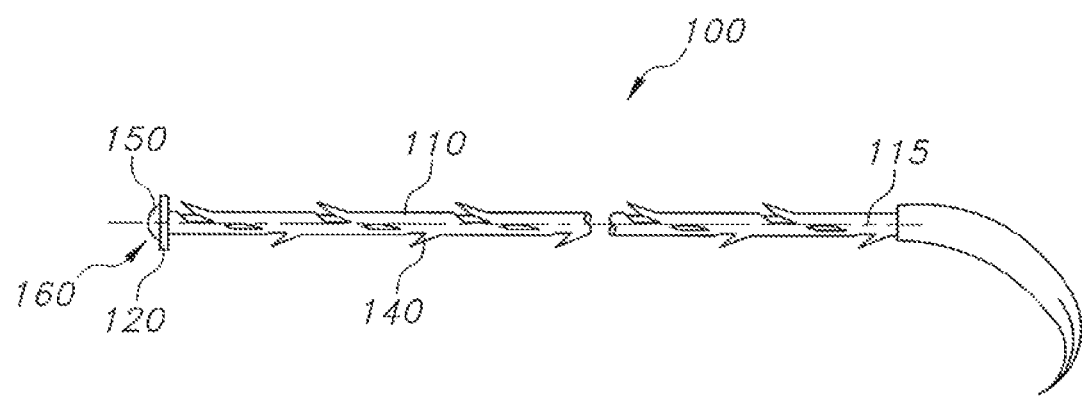
FIG. 1 depicts one exemplary suture of the present invention, which includes a termination feature at its distal end.

The present invention relates to sutures having a suitably strong end effector or termination feature at a non-needle end of the suture device. More particularly, the suture may include at least one retainer along its axial surface and may more desirably include a plurality of retainers. The suture may therefore be known as a self-retaining suture, such as those known and described in U.S. Patent Publication No. 2005/0267531 and U.S. Pat. No. 8,100,940, the entire contents of each of which are incorporated herein by reference. The retainers, if used, may be formed by any desired means, including cutting, shaping, molding, or other retainer-forming means. The description below will reference a suture having retainers formed on its surface, but a suture with no retainers (e.g., an "unbarbed" suture) may be used in the present invention.

The suture device may include multiple strands that are interconnected and therefore may include more than one trailing (or non-insertion, or non-needle end). Any or all of the trailing ends may include a termination feature of the present invention. As used herein, the terms "termination feature", "end effector" and "anchor" may be used interchangeably, and refer to the anchoring device at the trailing end of a suture. The present anchors offer a number of improvements over the prior attempts to prepare an anchoring element, including improved strength, and easier/less costly manufacturing parameters. The present invention forms an anchor without requiring the addition of materials (such as molten materials or other added elements) and also forms the end effector without the initial step of forming a knot prior to welding. The present anchor provides a strong fused termination device at the non-needle end of the suture, which adds stability and strength to the device. Further, the present invention allows for a number of varying shapes depending upon the desired use. The invention requires minimal thermally induced fiber property losses, since the formation need not expose the device to elevated temperature conditions. The present invention is capable of being formed in a continuous in-line processing methodology, which reduces manufacturing costs and allows repeated suture formation with ease.

In one embodiment of the present invention, a method of forming an anchor at a non-needle end of a suture is provided. The suture material includes at least one polymeric fiber, which has a first end, second end, and a body therebetween, where the body extends along a central longitudinal axis. The suture may include any material or combinations of materials that are suitable for use in surgical procedures, including polymeric and/or metallic materials. Further, the material of the suture desirably should include weldable materials, such as those materials that can be melted and/or deformed under the presence of energy, including ultrasonic energy. The suture material may be absorbable or non-absorbable, and may include, for example, polydioxanone, polyglycolic acid (PGA), polylactic acid (PLA), polycaprolactone (PCL), trimethylene carbonate, and copolymers thereof, as well as polypropylene, polyvinylidene fluoride, polyamide (nylon), polyester (polyethylene terephthalate), and other commonly used suture-forming materials.

The resulting suture has a length of suture extending between its first and second ends along its central longitudinal axis, and may have any cross-sectional configuration, including circular, elliptical, triangular, square or diamond-shaped, and the like. The outer surface of the suture body may have one or more retainers formed thereon, such as cut retainers as explained above. The suture may be of substantial length and stored in a spool or other housing which allows for easy removal of the suture strand without entangling the suture. For example, a spool of suture may include sufficient length of suture to form at least five termination feature-containing sutures, or at least ten termination feature-containing sutures, or at least fifty termination feature-containing sutures. The first end of the resulting termination feature-containing suture is the "insertion" or "leading" end, and may include a component to allow for insertion into tissue, such as a needle. The second end is the trailing or distal end. The first end (the insertion end) may be formed by severing a continuous length of suture material either before or after the formation of a termination feature of the present invention, and may include a needle secured thereto. Thus, at least two implantable sutures each including a termination feature (anchor) can be formed from a continuous length of suture formed in accordance with the methods described herein. Alternatively, the termination features may be formed on an individual length of suture, without the need for cutting the suture during the termination feature forming process.

The resulting termination feature-containing suture includes, at its second or trailing end, a termination feature. The termination feature generally includes a wound coil of suture, which has been subjected to energy sufficient to weld the suture coil to itself. The resulting termination feature has improved strength and can be used as an anchor to hold the suture in place after insertion in tissue, where the termination feature abuts the tissue into which the suture is inserted, providing an anchoring effect. One particular embodiment of the termination feature includes a termination feature which is free of any other components added to it, such as adhesives or strengthening agents. This embodiment may thus provide a termination feature that consists of the suture material and no added elements or components. The termination feature may be any shape, and may have an open interior (an "eyelet") or may have a closed structure. As noted above, the termination feature avoids the step of first forming a knotted structure and then subjecting that knotted structure to energy. The desired termination feature is formed into a coil, desirably while within the forming apparatus, and then that coil is subjected to energy to cause sufficient welding. It is understood that avoiding the need for initially forming a knot is not only more efficient but results in an anchor that is structurally different than knotted sutures.

In one method of forming a suture with a termination feature, the polymeric suture fiber is inserted in a cavity which contains a slotted pin element. The fiber is engaged with the slotted pin element within the cavity. Rotation and optional axial movement of the slotted pin element causes the fiber to wind about the circumference of the pin within the cavity forming a spiraled coil of fiber. Once a sufficient length of fiber has been wound into the cavity into a spiraled coil, the resulting coil of fiber is subjected to an energy source, such as ultrasonic forces. The transference of energy is achieved through the contact of a contact unit interface with the coiled material, and the coiled fiber is converted into fused polymer geometry having the general shape of the contact unit interface. The coiled fiber is preferably not entangled, that is, there are not overlapping coils such that the coil cannot be unwound without forming knotted regions. In the present invention, after the coil is formed, if the suture is pulled in either direction, the coil will unwind without knot formation.

The contact unit interface may include a welding horn and/or die. If desired, the suture material may be cut either prior to or after the formation of the end effector. In some methods, any excess suture material is severed prior to welding the termination feature. After the termination feature is formed, the remaining length of suture may be cut at a desired location, providing the length of suture with termination feature on its second end. This end that is left after cutting may be a cut that forms the leading end of the suture, onto which a needle or other insertion device may be secured.

The present invention also includes methods of packaging the inventive sutures, such that the suture and/or end effector does not become tangled or otherwise stuck to the packaging material.

As will be described in greater detail below, one type of an apparatus to form the termination feature of the present invention includes components such as a welding horn and base, the base including a winding pin and welding die. As used herein, the terms "down" or "downward" shall refer to the direction moving from the top of the welding horn toward the base of the winding post. The terms "down" and "downward" can apply to any component in the invention. Similarly, the terms "up" or "upward" shall refer to the direction from the base of the winding post to the top of the welding horn. The terms "up" or "upward" similarly can apply to any component in the invention. For example, if welding horn (200) is located in an "up" position, this means that the welding horn 200 has been moved in a direction that moves away from the winding post and welding die. Likewise, if the welding horn 200 is located in a "down" position, this means that welding horn 200 has been moved in a direction towards the winding post and welding die.

Referring to FIG. 1, one example of a self-retaining suture device 100 is illustrated. The suture device 100 in FIG. 1 includes a monofilament fiber 110, but it is understood that multi-filament sutures, including braided sutures and sutures having concentric filaments may be used. In FIG. 1, the suture 100 has been produced with a triangular cross section, but other cross-sections may be useful, including, for example, a circular cross-section. The monofilament fiber 110 has an outer surface, and may include a plurality of retainer elements 140 that have been cut into or otherwise formed on the outer surface of the fiber 110. Methods of cutting retainers 140 into a suture 100 are well-known, and include methods described in U.S. Pat. No. 6,848,152, the content of which is incorporated by reference herein in its entirety. Retainer elements 140 are not required, and the sutures of the present invention may be free of retainers on the suture.

The suture 100 includes first, leading end 115 (which may be termed the "proximal end" or "insertion end" and may optionally include a needle 130 secured thereto) and second, trailing end 150. The trailing end 150 of the fiber 110 is produced with a termination feature 120 (also referred to as an "end effector" or "anchor"), which is formed by the techniques outlined in this disclosure. The termination feature 120 desirably consists of the suture material itself, but may optionally include additives or strengthening materials before or after welding. In embodiments where the termination feature 120 is free of additives or strengthening materials, it is understood that trace materials of contaminants may be present, but that other materials other than the suture material itself are not intentionally added.

The termination feature 120 may be produced in a variety of geometries, including having a circular, triangular, rectangular (including, for example, diamond or square shaped), or other geometric cross section. Edges and corners of the termination feature 120 may be rounded or smooth, if desired. The termination feature 120 may have any desired thickness, and may have varying degrees of thickness throughout the termination feature 120 if desired. Further, there may be a tapered section extending from the outer surface of the suture fiber 110 to the termination feature 120. Various geometric configurations may be considered depending upon the use of the suture 100, including the location of placement in a patient, the type of tissue to be secured and the necessary strength of the fixation. In soft tissues, for example, where there is the potential for dilation of the suture tract, it may be desired to provide a termination feature 120 with a large bearing surface, oriented perpendicular to the central axis of the fiber 110. The termination feature 120 abuts the tissue into which the suture is inserted, having an anchoring effect.

FIG. 1 shows such a device, having a termination feature 120 that is oriented so as to be perpendicular to the central axis of the fiber 110. That is, the termination feature 120 has a major diameter that is perpendicular to the central axis of the suture fiber 110. The termination feature 120 may have a generally flat disk-like shape or it may have a curved distal end 160, as can be seen in FIG. 1. In firm tissues, it may be desirable to produce a termination feature oriented such that its diameter is substantially parallel to the axis of the fiber 110, such as a "lollipop-type" configuration seen in FIG. 11B. In some instances, it may be desirable to lock the suture back onto itself through the use of a looping mechanism, or with a termination that provides an engagement feature or open eyelet through which a suture may be passed.

The suture 100 may have any desired length and cross sectional diameter, including those described in greater detail below. It is particularly desirable that the cross-sectional diameter of the termination feature 120 be greater than the largest measured diameter of the suture 100. Thus, the ratio of the diameter of the termination feature 120 to the largest diameter of the suture 100 should be greater than 1.1:1, and may be up to about 10:1. More desirably, the ratio of the diameter of the termination feature 120 to the largest diameter of the suture 100 may be about 4:1 to about 10:1. The size and shape of the termination feature 120 will be described in greater detail below, but it is useful to provide a termination feature 120 that is large enough to act as a suitable anchor, while at the same time having a termination feature 120 that is sufficiently small to be manufactured and packaged appropriately. As used herein, the term "diameter" does not necessarily refer to a circular cross-section, and the term "diameter" can refer to the largest distance from opposing ends of device, such as opposing corners of a square.

The termination feature 120 is desirably composed of the suture fiber 110, which has been wound and subsequently formed into a solid structure, such as through the application of energy. As noted, it is particularly preferred that the termination feature 120 be free of any additional materials, however, it may be desired to include one or more compositions that are capable of filling in any potential gaps in the wound fiber and/or strengthen the final welded termination feature 120. As will be described below, the fiber 110 is wound into a coil while the suture is contained in the welding apparatus, and is then welded to form the termination feature 120. In this method, there is no pre-forming step, such as the formation of a knot or other structure, prior to winding and welding. The wound portion of the fiber 110 may include a plurality of retainers 140 or it may be free of retainers 140.

Figure 2:
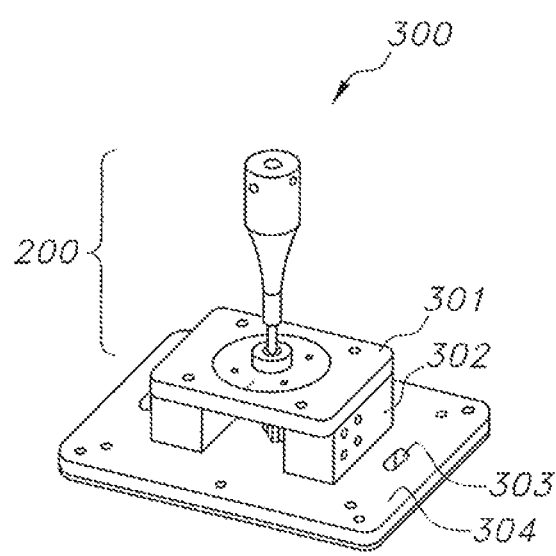
FIG. 2 depicts one embodiment of an assembled welding horn and welding nest.
Figure 3:
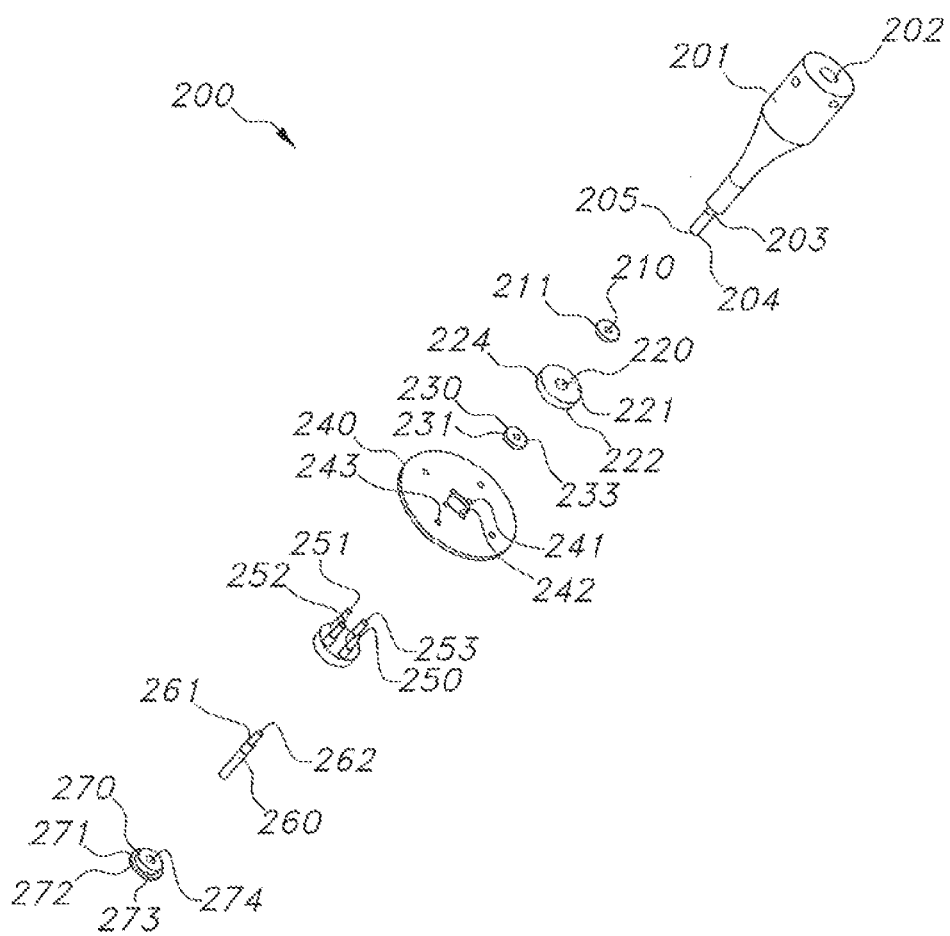
FIG. 3 depicts an exploded view of the components of a welding horn, which may be useful in the present invention.

Referring to FIGS. 2 and 3, an apparatus for manufacture of the suture 100 and termination feature 120 is depicted. The apparatus may include a welding horn 200 and a welding nest 300 (welding nest 300 may be considered the "base" of the welding apparatus). The welding horn 200 is designed to mate with the welding nest 300 to provide the termination feature 120 as desired. The welding nest 300 may include a raised mounting plate 301 that is mounted to a top side of support pillars 302. In the depicted Figure, two pillars 302 are shown, but more than two support pillars 302 may be used if desired. Each pillar 302 has an upper end and bottom end, the upper end being secured to the mounting plate 301. The bottom end of the pillar 302 is mounted to a nest base plate 304. The pillars 302 may be detachable from either the mounting plate 301 or the nest base plate 304. The nest base plate 304 may include a means to attach the welding nest 300 to a secure surface for welding. For example, the nest base plate 304 may include a series of through bore mounting holes 303 that enable attachment of the welding nest 300 to a supporting structure during use.

Referring to FIG. 3, a number of components in the welding assembly are depicted. This Figure includes a number of individual components that are described herein in detail, but it is understood that modifications of assembly may alter or remove one or more of the components described herein without modifying the function and use of the assembly. The assembly seen in FIG. 3 includes an ultrasonic horn 201, which is a length and design that is suitable to the frequency of the particular ultrasonic generator that has been selected. Frequencies of from about 15 kHz to about 40 kHz, and more specifically about 20 kHz may be useful in forming the termination feature 120 of the present invention, and the ultrasonic horn 201 of the invention should be suitable to deliver the intended frequencies. The ultrasonic horn 201 may be produced with a threaded bore 202 at its upper end that is utilized to attach the horn to an ultrasonic welding booster/transducer assembly (not shown). The horn 201 has an axis that runs through its length from the threaded bore 202 to an ultrasonic horn tip 205.

The horn 201 may be any desired shape or configuration, including a cylindrical shape, or having a cross-section that has varying geometry. Preferably, the horn 201 is tapered, having a larger cross-sectional diameter at its upper end and tapering to a smaller cross-sectional diameter at its lower end. The horn 201 may include a stepped elliptically shaped cylindrical wall 203. In a preferred embodiment, the ultrasonic horn 201 is produced with a reduced diameter shoulder 204 that is intended to engage with an insert ring 210 during the welding process. The insert ring 210 is desirably polymeric material, but may be metallic or include other materials if desired. An ultrasonic horn tip 205 is disposed at the lower end of the horn 201. The ultrasonic horn tip 205 is sized and shaped to fit within a receiving bore 222 of a welding die 220. The horn tip 205 and the welding die 220 are sized and shaped so as to provide the desired structure and geometry of the termination feature 120. In use, the coiled suture fiber is placed between and within the horn tip 205 and welding die 220, and then energy is applied.

It may be desired to include an elastic element in contact with the welding die 220, such as beneath the welding die 220, so as to allow the welding die 220 to remain engaged with the horn tip 205 during the application of energy. As the horn 201 oscillates vertically, the spring force acting upon the die helps to maintain the welding die 220 in contact during the weld cycle. It has also been found that if the welding die 220 remains in substantially tight engagement with the horn 201 during the cycle, that the welding of the upper coils of fiber may be diminished and the weld that is produced is similar in appearance to those produced within a cavity in the face of the horn. Preferred welding conditions are achieved through the addition of a frictional drag component to the cage leg elements. The necessary frictional drag component of die movement ensures that the welding die 220 does not vibrate in unison with or in exact frequency with the ultrasonic horn 201. While the elastic element and drag elements may be achieved through the use of elastic material and ball plungers, the use of springs, air or other springs, as well as spiral displacement of the welding die 220 or the use of external damping elements such as brake or shock absorber style elements are also feasible. In one embodiment, the device includes an elastic element in combination with a separate damping element, which allows the welding die to vibrate or otherwise move out of synchronization with the ultrasonic horn during the cycle.

The welding die 220 is placed in a location that may secure the suture fiber 110 between it and the horn tip 205 in use. Thus, the welding die 220 may be disposed in a coaxial configuration with the horn 201, such that if the horn 201 and/or the welding die 220 are moved in an axial fashion (e.g., up and down), a suture fiber 110 may be placed into the space therebetween.

Figure 4:
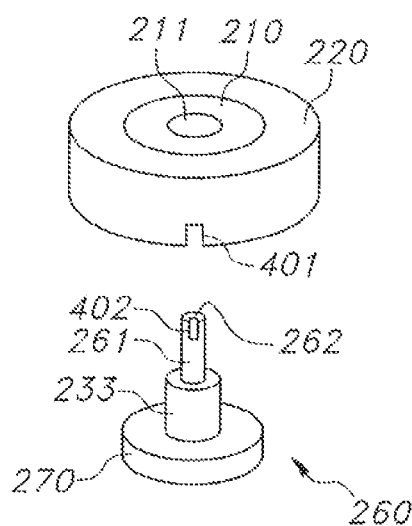
FIG. 4 depicts a welding die and winding pin assembly in separated configuration.

The welding die 220 may include a receiving bore 222 that is sized and shaped to match the desired edge shapes and sizes that are desired for the final termination feature 120 to be formed. The external size and shape of the ultrasonic horn tip 205 is sized and shaped to mate with the receiving bore 222 so as to form the final termination feature 120. Additionally, the welding die may include a central counter bore 224 that is sized to receive insert ring 210. As can best be seen in FIG. 4, the outer diameter of the insert ring 210 is sized to fit tightly into the central counter bore 224 of the welding die 220. The insert ring 210 and/or the welding die 220 may include a feature or series of features on its underside (not seen in FIG. 4), which will engage with posts 252 of guide unit 250 for secure attachment. For example, the welding die 220 may include a plurality of through bores 221 as seen in FIG. 3. FIG. 4 shows the relationship between welding die 220 and winding pin 260. As can be understood, the shapes and sizes of the die and horn components will dictate the resulting shape and size of the termination feature 120.

The various components described above may be made from any desired materials, provided that the materials selected are suitable for withstanding ultrasonic frequencies and delivering to the suture 100 to provide the termination feature 120. For example, the insert ring 210 may be manufactured of any suitable polymer material including polyolefins, polyesters, pvdf, Teflon based materials, PEEK and other suitable polymers. Alternatively, the insert ring 210 may be made from metallic materials with a lower hardness than the material utilized to produce the ultrasonic horn 201, such as bronze, aluminum, and other metallic materials having a lower hardness than the ultrasonic horn 201. The ultrasonic horn 201 may be made from metallic materials, such as titanium, aluminum, or stainless steel.

The welding nest assembly 300 includes a fixture plate 240, which is placed and held within the mounting plate 301, and may be removable or may be secured in the mounting plate 301. The fixture plate 240 may include a central counter bore 242. The welding nest 300 may also include a post insert plate 230. The outer diameter of the post insert plate 230 is sized and shaped to fit snugly within the counter bore 242 located within the fixture plate 240. The post insert plate 230 may be removably or permanently secured to the fixture plate 240 and may include a series of through bores 241 to receive posts 252 of guide unit 250. The post insert plate 230 may additionally incorporate a central through bore 233. The central through bore 233 is sized to slidably receive a winding pin 260.

The fixture plate 240 may be produced with a means to secure the fixture plate 240 to the mounting plate 301. For example, as can be seen in FIG. 3, fixture plate 240 includes several through threaded bore features 243 that are located about the perimeter of the plate 240. These threaded through bores 243 are utilized to attach the fixture plate 240 to the mounting plate 301. The central portion of the fixture plate 240 may be produced with a through bore for passage of the winding pin 260.

The assembly may optionally include a guide unit 250, which may include a through bore 251 that is slidably engageable with the winding pin 260. Extending from the upper surface of the guide unit 250 are a plurality of posts 252 that may have a shouldered or larger diameter region 253. The posts 252 are arranged and sized to mate with through bore holes 243 in the fixture plate 240. In some embodiments, there may be four posts 252, but any desired number of posts may be included. The shouldered or larger diameter region 253 of post 252 is desirably larger in diameter than the through bore holes 243 in the fixture plate 240 to provide a secure hold. The winding pin 260 may have a tapered inner through bore 262. Further, the winding pin 260 has a first end 263 and a second end 261, the first end 263 having a larger outer diameter than the second end 261, and the first end 263 optionally being coupled with a winding knob 270. The second end 261 of winding pin 260 may be slidably engaged with the central opening of the post insert plate 230.

FIGS. 4-10 show examples of a useful welding die, post insert, and winding pin, as well as depict one method of the formation of a termination structure 120 of the present invention. FIG. 4 illustrates a welding die assembly 220 in an "up" position relative to the welding post 233 and the winding pin 260. The winding pin 260 may have a hollow tapered bore 262 that exits at the second end 261 of the pin. The hollow interior of the winding pin 260 is desirably sized to have a larger diameter than the diameter of a suture fiber 110 to be used. The suture fiber 110, prior to formation of a termination feature, can therefore be fed through the interior of the winding pin 260 without restriction or damage. The internal diameter of the pin 260 may be tapered, ending at a notch 402 at the second end 261 of the pin 260. The interior diameter of the pin 260 may be smaller at the second end 261 of the pin 260 than on the first end 263 of the pin. This inner taper may be useful in enabling smooth feeding of a suture fiber into the pin 260. Welding die 220 may have a partial channel or notch 401 on its downward side, with the channel 401 being sized sufficiently to allow passage of a suture fiber 110 therethrough.

Figure 5:
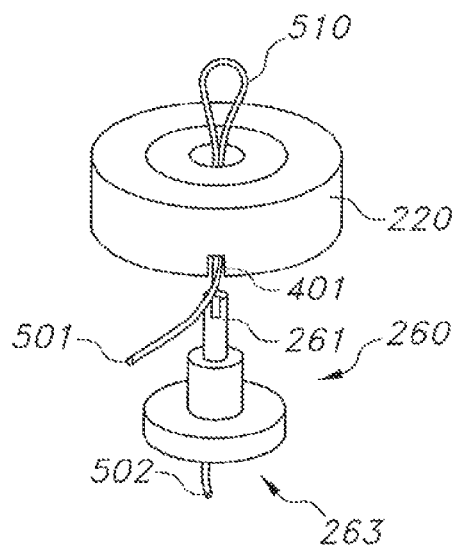
FIG. 5 depicts one step in feeding a suture into the welding die assembly.

Referring now to FIG. 5, one method of feeding a length of suture into the winding pin is depicted. In this embodiment, a length of suture 510 may be inserted through the first end 263 of the winding pin 260 and fed "upward" towards the second end 261 of the winding pin 260. Since there is no pre-formed knot or other structure, the suture 510 is capable of being fed through winding pin 260 and out second end 261. The suture 510 may then be bent as illustrated, and the first end 501 of the suture 510 may be passed through the channel 401 and through the notch 402. Second end 502 of the suture 510 remains sticking out through the first end 263 of the winding pin 260. Although the die 220 is illustrated in a separated condition from the winding knob 270, the die 220 may be located in a nested position on top of the winding knob 270.

Figure 6:
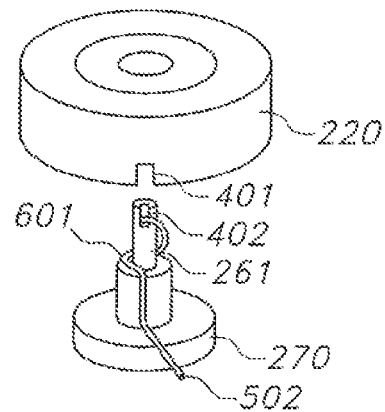
FIG. 6 depicts another step in feeding a suture into the welding die assembly.
Figure 7:
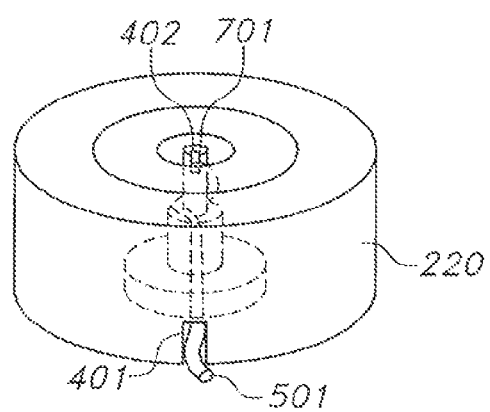
FIG. 7 depicts the suture fed into the welding die assembly.

Referring now to FIGS. 6 and 7, the rotation of the winding pin 260 is illustrated. It should be noted that the welding die 220 is illustrated in the "raised" position only for the sake of providing visualization of the suture fiber 510 as it would form a wrapped geometry 601 when inside of the welding die 220. In use, the welding die 220 may be lowered (or, alternatively, the winding pin 260 raised) so that the winding pin 260 is located within the interior of the welding die 220. FIG. 7 illustrates the position of the winding pin 260 relative to the top of the welding die 220 during winding, with the welding die 220 in the "down" position for the winding operation to be conducted. The winding pin 260 is disposed within the interior of the welding die 220, such that the second end 261 of the winding pin 260 is nearly flush with the upper region of the welding die 220 during the winding operation. This flush configuration and the location of the winding pin 260 in this configuration is identified as reference numeral 701. The suture fiber 510 wrapping is illustrated as a dashed line within the welding die 220. In this configuration, the winding pin 260 and welding die 220 are in the "winding position". As can be seen, the first end 501 of the suture fiber 510 extends out through the channel 401 and notch 402. Although not seen in FIG. 7, the second end 502 of the suture extends through the bottom of the winding pin 260.

Figure 8:
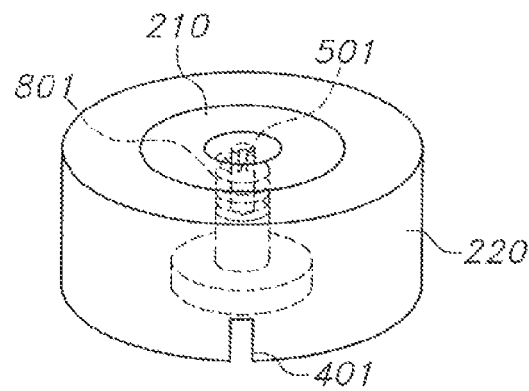
FIG. 8 depicts the suture in wound fashion in the welding die assembly.

Referring now to FIG. 8, the first end 501 of the suture fiber 510 has been wound in the welding die 220 and is illustrated as coil 801 wrapped around the winding pin 260. Alternatively, the first end 501 maybe left partially inside of the channel in the welding die 220 and may be trimmed from the coil 801 either before application of energy to the coil 801, during the down stroke of the ultrasonic horn 201, or after welding is complete. Similarly, the second end 502 of the suture may be cut at any desired time in the welding process or it may remain unsevered until the welding is complete. The length of suture 510 desired is achieved by cutting the second end 502 at a desired length away from the termination feature 120. More desirably, the second end 502 is cut after welding is complete, thus forming a resulting suture having a termination feature.

Figure 9A:
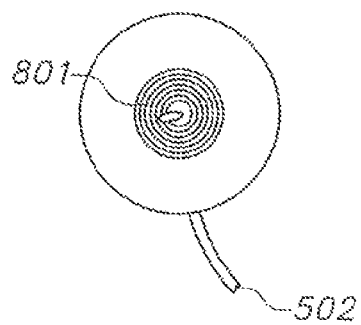
FIGS. 9 and 9A depict the suture in wound fashion with welding die separated from winding pin.
Figure 9:
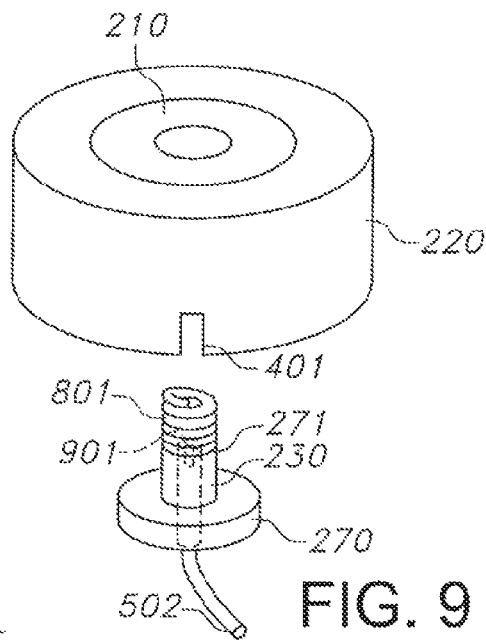

Referring now to FIG. 9, the coiled fiber 801 is illustrated, after winding is complete. The welding die 220 has been lifted in the Figure to allow viewing of the coil 801 only, but it is noted that in use, the welding die 220 would not be removed during use as the interior of the welding die 220 helps to maintain the coil 801 in its coiled configuration. As seen in FIG. 9, the winding pin 260 has been lowered to a "welding position" (identified by reference numeral 901) by retracting the winding pin 260 in the "downward" direction. The winding pin 260 is lowered a sufficient length, such as until the notched end 402 of the winding pin 260 is substantially flush with the top surface of the post insert plate 230. In an alternative embodiment, the winding pin 260 may remain at least partially in an "up" position relative to the post insert plate 230. This alternative arrangement may be useful, for example, in creating an open eyelet structure within the termination feature.

Figure 10:
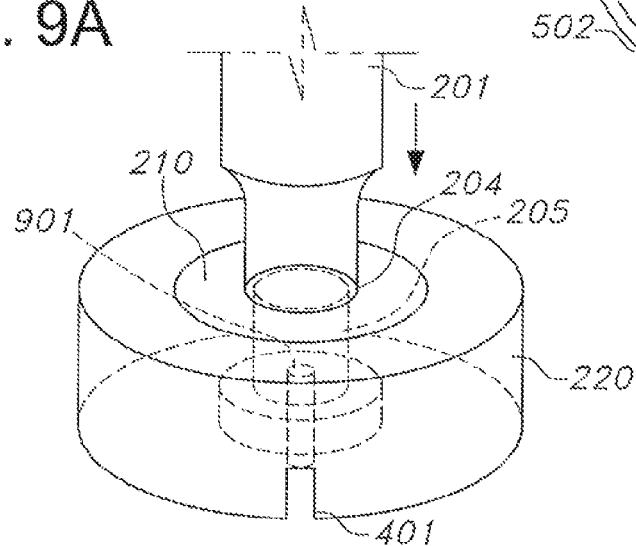
FIG. 10 depicts a welding horn in the downward, welding position.

Referring now to FIG. 10, the ultrasonic horn 201 is lowered into the welding position and is subsequently energized. The operation illustrated in this figure involves the downward motion of the welding die 220 due to contact with the shoulder 204 of the horn 201 with the insert ring 210 during the welding cycle. Therefore, the welding die 220 may be movable relative to the welding post 270. This mode of action enables the adjustment of a gap between the ultrasonic horn tip 205 and the top of the post insert plate 230. The ultrasonic horn tip 205 may be at least substantially, and desirably fully within the open interior of the welding die 220, however, the wall of the tip cylinder 205 does not necessarily contact the inner bore 211 of the insert ring 210. In preferred embodiments, a clearance of about 0.0005-0.002 inches between the side wall of the horn tip 205 and the interior wall of the insert ring 210 is desired to prevent contact.

Thus, in the aforementioned embodiment of the method of formation of a termination structure 120, an assembly including a welding die assembly 220, winding pin 260 extending therethrough and axially movable through the welding die assembly 220, and welding horn 201 are provided. In this embodiment, the welding horn 201 and welding die assembly 220 are moved so as to be separated from each other, and winding pin 260 is contained within the middle open space of the welding die assembly 220. A suture fiber 510 is fed through the inner open interior of the winding pin 260 such that the suture fiber 510 extends out of the second end 261 of the winding pin 260. The winding pin 260 is rotated axially and/or the suture fiber 510 is moved circumferentially about the outside of the winding pin 260 to create a coil 801. A winding knob 270 may optionally be used to effectuate winding.

After the coil 801 is formed, the winding pin 260 may be axially moved in a downward position (e.g., moved in a direction away from the welding horn 201) or it may remain in the "up" position. The welding horn 201 and welding die assembly 220 are brought closer together, such that the coil 801 is entrapped within the space provided by the welding horn 201 and welding die assembly 220. Excess suture fiber 510 may be trimmed from the coil 801 either before application of energy to the coil 801, during the down stroke of the ultrasonic horn 201, or after welding is complete. Energy is applied to the coil 801 and optionally pressure and/or temperature increases may be applied to the coil 801 as well. The suture fiber 510 is allowed to at least partially melt and then the energy (and optional pressure and temperature) are removed, and the now-welded coil 801 is allowed to solidify. The resulting suture 510 now has a suitable termination feature 120 on its end. The suture fiber 510 may be severed at any desired location to provide a desired length of suture.

The welding end of the ultrasonic horn tip 205 is designed to have any of a number of geometries, including flat, conical, spherical convex, spherical concave and polyhedral geometries. It may alternatively have a textured configuration. It has been found that the use of a spherical concave tip design provides lateral compaction of the coiled fiber 801 during the welding cycle. The coiled fiber orientation, coupled with the lateral compaction, provides the transmission of the ultrasonic energy through the tangential contact edges of the coiled fiber 801 to form an essentially solid end termination for the suture 510. In contrast to previous methods in which a knot is first tied in the suture material, this mode of welding restricts the creation of crossing fibers or of a random orientation of fibers, which can create undesirable notch effects in the termination feature. The inventive methods thereby increase tensile strength of the resulting termination feature 120 and provide a structurally different termination feature 120. In addition, the present methods avoid the need for pre-welding steps such as tying a knot, which not only avoids the risk of malfunction, but also allows for easier and quicker processing of sutures.

Figure 11A:
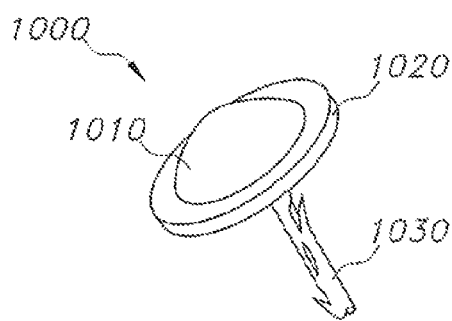
FIGS. 11A-11D depict various termination features.

As noted above, the termination feature 120 may be produced in multiple geometries, depending upon the purpose and desired look and feel. The size and shape of the termination feature 120, as well as any surface texture or configuration, may vary depending upon the desired suture. Various termination feature configurations are depicted in FIGS. 11A-11D. FIG. 11A shows a termination feature 1000 having a large tissue bearing surface. The termination feature 1000 includes a raised surface 1010, such as a bulbous or convex surface, and includes a round circumference 1020. The embodiment of FIG. 11A has an orientation that is perpendicular to the longitudinal axis of the suture 1030. The suture 1030 extends substantially from the center of the termination feature 1000. FIG. 11A may be modified such that the suture 1030 extends from a side of the circumference 1020, giving a "lollipop" type configuration. The thickness and the cross-sectional diameter of the circumference 1020 of the termination feature 1000 may vary as desired.

Figure 11B:
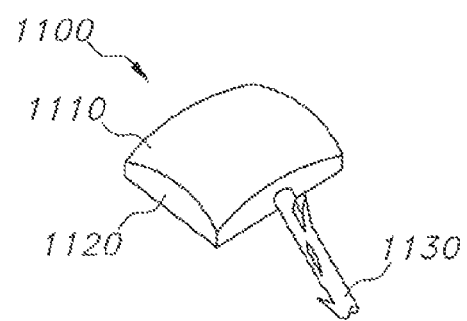

FIG. 11B shows an alternate configuration with a raised surface 1110, but the termination feature 1100 has a square or rectangular circumference 1120. The corners of the circumference 1120 may be rounded or they may have sharp angles. The suture 1130 in this embodiment extends from the outer circumference 1120 of the termination feature 1100, similar to a "lollipop" configuration. FIG. 11B may be modified such that the suture 1130 extends from the center of the termination feature 1100. The thickness and the cross-sectional diagonal of the circumference 1120 of the termination feature 1100 may vary as desired.

Figure 11C:
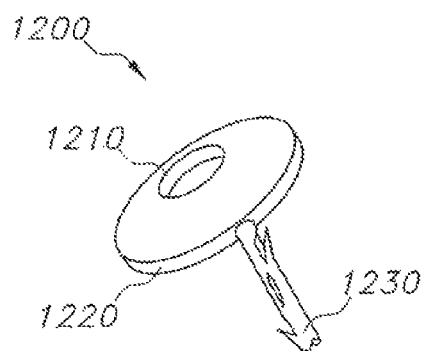
Figure 11D:
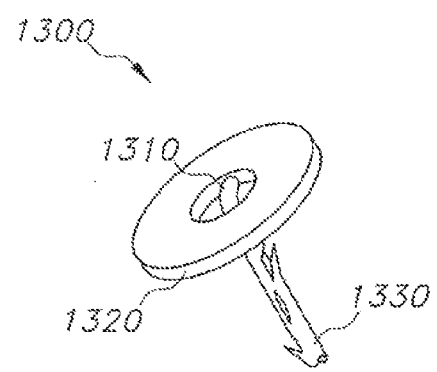

Alternatively, the termination feature may include an eyelet or open configuration, such as that seen in FIGS. 11C and 11D. FIG. 11C shows a termination feature 1200 having a central eyelet 1210, and a rounded circumference 1220. It is understood that the circumference 1210 need not be rounded and may have other geometries. In this configuration, the suture 1230 extends from the side of the circumference 1220, such as a lollipop configuration. The size of the eyelet 1210 may vary as desired, but it is desirable that the diameter of the eyelet 1210 be larger than the cross-sectional diameter of the suture 1230. The interior sides of the eyelet 1210 may be substantially smooth and may be rounded if desired. The eyelet 1210 need not be round and may alternatively be different geometric shapes. FIG. 11D shows a similar termination feature as in FIG. 11C, but the termination feature 1300 of FIG. 11D includes an eyelet 1310, where the suture 1330 extends from the interior of the eyelet 1310. The termination feature 1300 also includes an outer circumference 1320. As with the other termination features, the termination feature 1300 need not necessarily have a rounded circumference, and the eyelet 1310 need not have a round configuration. The size of the eyelet 1310 may vary as desired, but it is desirable that the diameter of the eyelet 1310 be larger than the cross-sectional diameter of the suture 1330.

The termination feature (1200, 1300) may be produced with eyelet features 1220 or 1320 through modifications to the welding process as described previously. For example, the production of a termination feature (1200, 1300) with an eyelet (1220, 1320) may be formed by leaving the winding pin 260 in an at least partially "upward" position during welding, that is, the winding pin 260 may remain at least partially within the interior of the welding die 220 during the welding process (during the application of energy). The winding pin 260 therefore creates a region within the coil during welding. After welding, the pin 260 may be lowered and reveal the anchor including an open eyelet.

The various configurations for termination features, including shapes, sizes, cross-sectional diameters, presence of thicker or thinner regions, or textured surfaces may be produced through the use of a welding die 220 and ultrasonic horn tip 205 that includes the desired shapes, sizes, textures. Alternatively, the termination features (e.g., 120) may be subjected to secondary processing such as stamping, cutting, reforming, annealing, surface treating, abrading, or other mechanical or chemical treatments to produce different geometries, shapes, textures or other characteristics desired. In some embodiments, after the suture is formed with termination feature 120, the suture and/or termination feature may be subjected to a heat sterilization treatment, which may provide some annealing to the suture and/or termination feature 120. Such heat treatment may be at temperatures of from about 40° C. to about 80° C., and more specifically from about 50° C. to about 60° C., and most desirably about 55° C.

Figure 12:
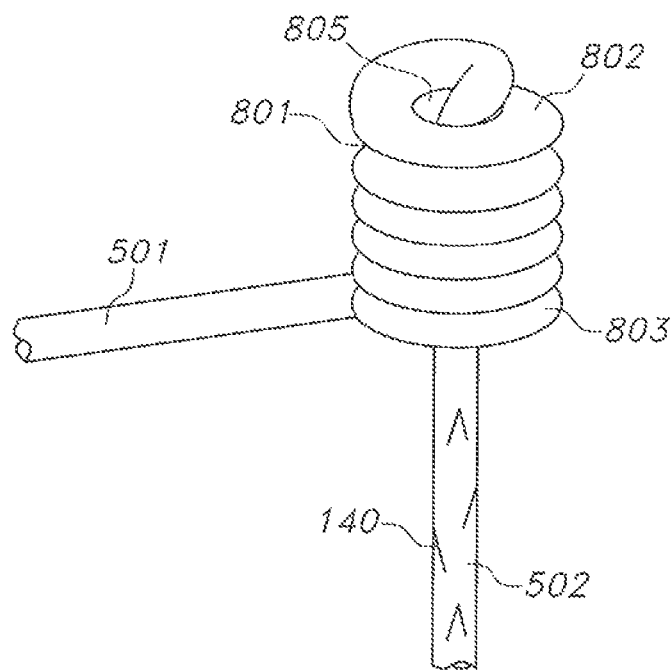
FIG. 12 is a suture coil formed by an embodiment of the present invention.

Referring to FIG. 12, the suture coil 801 that is formed through the winding process previously illustrated, for example, in FIGS. 5-9 is illustrated in the absence of the winding fixture. The coil 801 is formed with a distal coil end 802, which is terminated by the second end of the suture 502 bending inward towards the center point of the coil and downwards passing through an inner cavity 805 of the formed suture coil 801. The coil 801 has an opposing proximal end 803, which terminates with a first end of the suture 501 bending outwards away from the diameter of the suture coil 801. The inner diameter of the cavity 805 may be larger than the cross-sectional diameter of the suture 501 passing through the cavity 805, due to the use of a hollow pin during the winding operation. This difference in diameter may be equivalent to the doubling of the wall thickness of the hollow pin.

Figure 13:
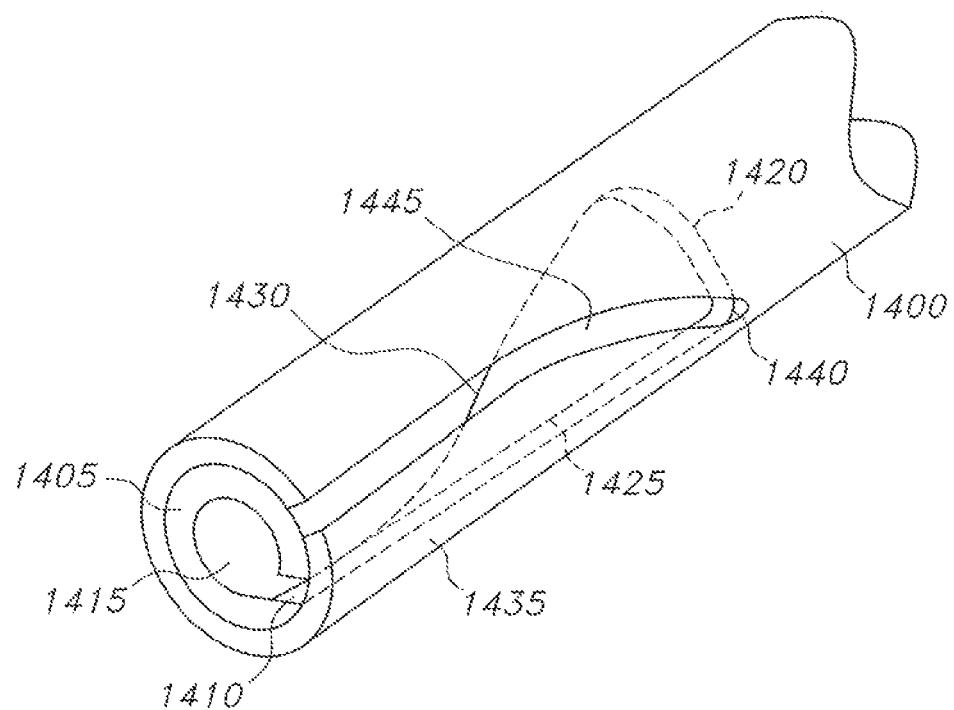
FIG. 13 is an alternative winding pin.

Referring to FIG. 13, an alternative style of pin for winding a fiber from a location above the welding die, the benefits of which will be discussed later, is presented. In this embodiment, pin 1400 includes two concentric cylindrical elements, an inner cylindrical element 1405 and outer cylindrical element 1435. Each of the cylindrical elements has an interior that is at least partially open, and defined by an outer wall. The outer surface of the inner cylindrical element 1405 is at least partially in contact with the inner surface of the outer cylindrical element 1435. The inner cylindrical element 1405 includes a slot 1410. The slot 1410 extends from an open end 1415 of the pin 1400 at least partially along the length of the inner cylindrical element 1405. The upper edge 1420 of the slot 1410 may be greater in width than the width of the slot 1410 at a region closer to the open end 1415 of the inner cylindrical element 1405. A first edge 1425 of the slot 1410 extends between the open end 1415 of the pin and the upper edge 1420 of the slot 1410 in a relatively straight line perpendicular to the central axis of the pin 1400. A second, opposing edge 1430 of the slot 1410 extends in an at least curvilinear direction between the open end 1415 of the pin and the upper edge 1420 of the slot 1410.

In this embodiment, the upper end of the inner cylinder 1405 is attached to a winding system driver (not shown). The outer cylinder 1435 is illustrated with an outer slot 1440, which extends at least partially along the axial length of the outer cylinder 1435, and may have a curvilinear shape as it extends along the axial length of the outer cylinder 1435. The degree of curvature of the outer slot 1440 may vary as desired. In use, rotation of one of the cylinders (1405, 1435) relative to the other cylinder creates a passage 1445 of varying size and length depending upon the shape of the slots (1410, 1440) and the degree of curvature of each. As the cylinders (1405, 1435) are rotated relative to each other, the size and shape of the passage 1445 extending from outside the pin 1400 to the interior of the pin is changed.

While the particular embodiment shown in FIG. 13 utilizes slots each having curvilinear features or geometries, it is understood that combinations that utilize straight slots in combination with or instead of curvilinear slots are also feasible, and the use of a straight slot in the outer cylindrical element with a curvilinear slot in the inner element may be used. The preferred embodiment utilizes an inner cylindrical element with a slotted feature that is primarily cut in a straight line. The use of a straight slot may be effective to maintain the maximum strength of the inner cylindrical element, since it is smaller in diameter than the outer cylinder, while simplifying the removal of the wound fiber from the pin 1400 prior to welding. While the inner cylinder 1405 has been illustrated as a hollow cylinder with a slot, a solid pin with a slot formed in the side of the pin extending away from the open end 1415 of the pin may be preferable.

Figure 14:
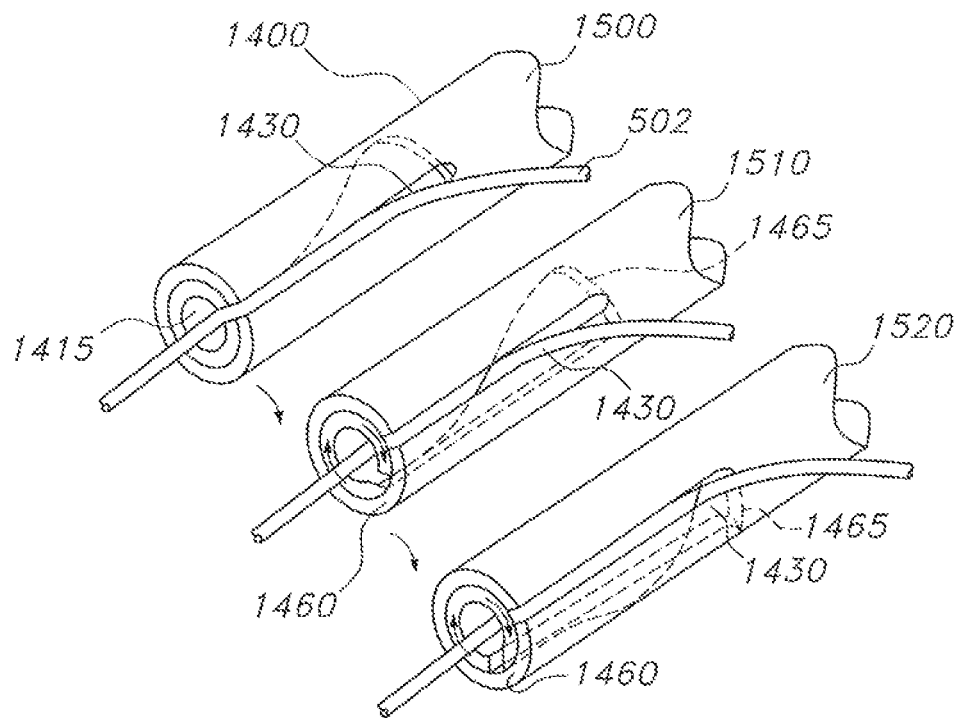
FIG. 14 depicts a winding pin of FIG. 13 in use in three sequential steps.

Referring now to FIG. 14, operation of the slotted winding pin 1400 (of FIG. 13) is illustrated in at least three sequential steps (1500 being the first step, 1510 the second step, and 1520 the third step). The first step 1500 of the winding process is initiated in an open position to receive the fiber 501. In this position, the two cylindrical components (1405, 1435) are rotated relative to each other to align the inner slot 1410 and outer slot 1440 to provide a passage for the fiber 501 to lay into the pin 1400 at the open end 1415 of the pin. The fiber 501 is placed into the device such that at least a portion of the fiber 501 is contained within the interior of the pin 1400 and at least a portion of the fiber 501 extends out through the open end 1415 of the pin, and at least a portion of the fiber 501 extends out of the pin 1400 through the passage 1430 formed by aligning the slots (1410, 1440).

In the second step (1510), the inner cylinder 1405 and outer cylinder 1435 are rotated with respect to each other so as to cause the slots at the open end 1415 of the pin to no longer align with each other. In this position, there is a passage 1430 remaining between the inner cylinder 1405 and outer cylinder 1435, but there is no passage 1430 at the open end 1415 of the pin 1400. Thus, there is a closed end 1460 at the open end 1415 of the pin 1400. The fiber 501 is drawn slightly proximally towards the termination position 1465 of the outer slot 1440. As the cylindrical components (1405, 1435) are rotated with respect to each other further about their axes, the passage 1430 size and/or length is reduced further. In this position (embodied by step 1520), the fiber 501 exits from within the pin 1400 through a reduced size/length passage 1430. This passage 1430 may be axially located at a distance from the open end 1415 of the pin that enables the formation of a sufficient quantity of fiber coils, so to produce the desired termination feature.

Once the fiber 501 is in this final position and the passage 1430 is sized to the desired configuration by rotating the inner and/or outer cylinder with respect to each other, the winding operation may be performed to wind the fiber 501 about the pin 1400. Once the fiber 501 winding is completed, the cylindrical components (1405, 1435) may be rotated back to the position to create the open passage 1430 extending to the open end 1415 of the pin, and thereby creating a fully open passage 1430. The winding pin 1400 may then be removed from the resulting coiled fiber from the upper (distal) end of the coil (802, in FIG. 12). This action may be assisted through the use of a stripper ring to facilitate the removal of the pin 1400 without disturbing the coiled fiber 801 within the die.

Figure 15:
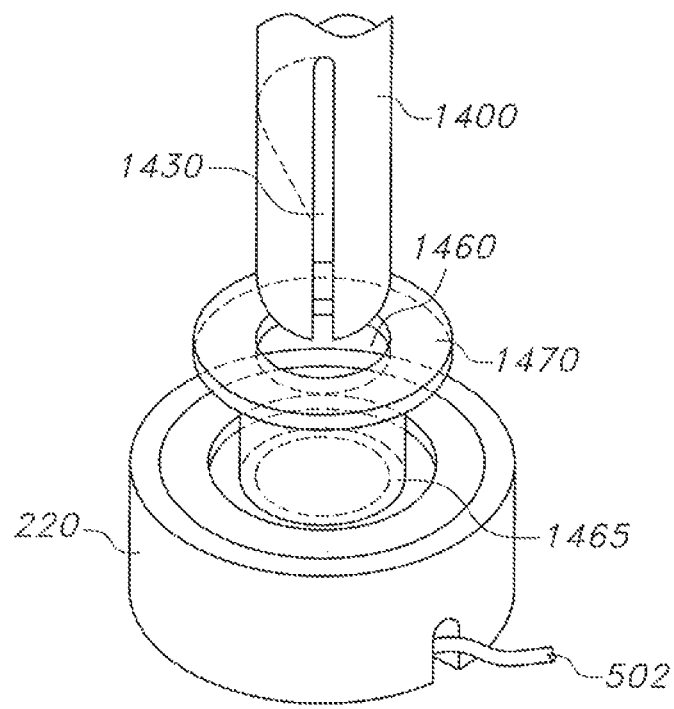
FIG. 15 shows a winding pin with slots aligned.

Referring now to FIG. 15, the winding pin 1400 with the slots aligned and open (creating passageway 1430 that extends to the open end 1415 of the pin) is positioned over a post insert plate. An intermediary slidable stripper 1460 may be positioned between the winder pin 1400 and the welding die 220. The stripper 1460 is produced with a lower barrel portion 1465 that is sized to fit within the upper portion of the welding die 220 and substantially fills the cylindrical space between the outer surface of the winder pin 1400 and the inner diameter of the welding die 220. The stripper 1460 may optionally be produced with a flange like region 1470 for use in lifting or lowering the stripper 1460. The inner diameter of the stripper 1460 is sized to be in slidable engagement with the outer surface of the winding pin 1400.

Figure 16:
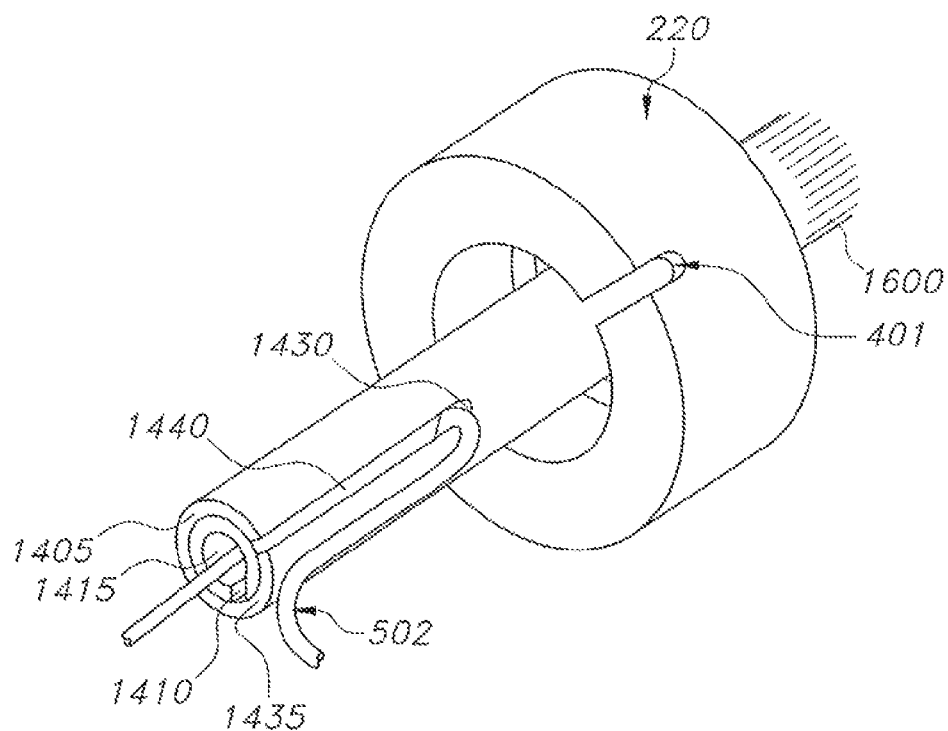
FIG. 16 shows a winding pin with fiber loaded therein.

FIG. 16 shows the winder pin 1400 the fiber 501 loaded within the open center of the pin 1400 such that one end of the fiber 501 extends through the open end 1415 of the pin 1400 and a second end of the fiber 502 extends through the passage 1430 formed by alignment of the two slots (1410, 1440). The welding die 220 is shown in a retracted position, prior to the winding operation occurring. The slot 401 in the base of the welding die 220 is also illustrated. In some embodiments, the winding pin 1400 may be attached to an engageable feature 1600, such as a drive spline, gear, v-belt, or frictional drive element. The engageable feature 1600 may be utilized to spin the welding pin 1400.

Figure 17:
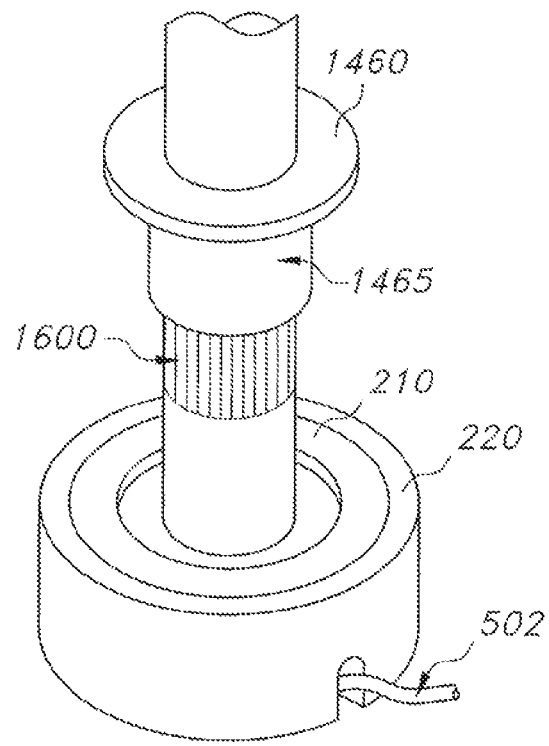
FIG. 17 depicts the winding pin in a winding position with fiber loaded therein.

FIG. 17 illustrates the winder pin 1400 in the winding position, with the fiber 501 loaded into the winder pin 1400 as described above, and the welding die 220 located about the winder pin 1400. The stripper 1460 is in the "up" position. The next step in the welding operation is to move the stripper 1460 downward within the open bore of the welding die 220 prior to the winding cycle initiation.

Figure 18:
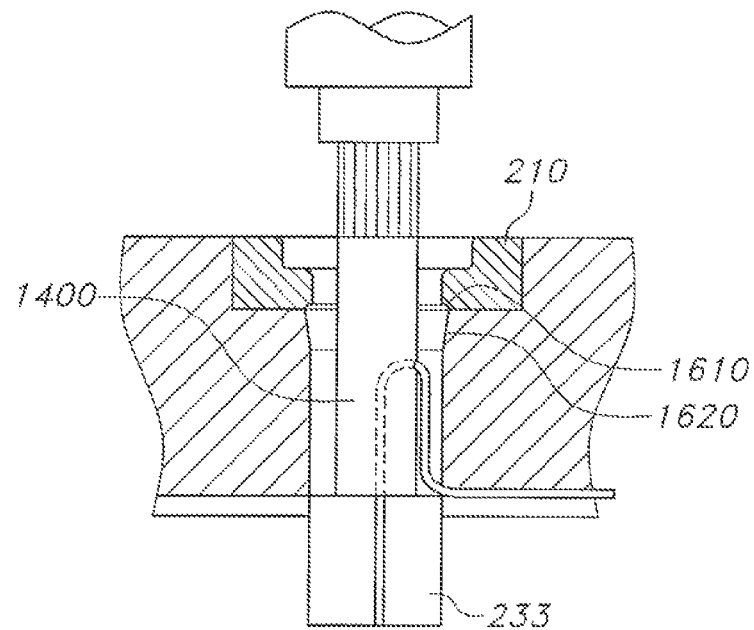
FIG. 18 shows a partial sectional view of a winding pin of the present invention.

As seen in FIG. 18, the winder pin 1400 is again presented, however, the view is a partial sectional view whereby the welding die 220, insert ring 210 and welding post 233 are sectioned to reveal the inner cavity of the die 220, with the pre-winding positioning of the fiber 501. Additionally, the details of the inner cavity profile are also visible. The insert ring is bored through with a stepped diameter. This stepped profile remains in contact with an ultrasonic horn during the welding cycle, described above. Additionally, there is a tapered region 1620 located at the top of the through bore of the welding die 220, which mates up to a radiused edge of the insert ring 1610 to form an undercut feature in the mated components. The undercut feature provides a point of contact with the pre-weld coiled fiber (e.g., 801) when the stripper 1460 is removed. This undercut prevents the stressed coiled fibers from relieving themselves of the internal post coiling stresses prior to welding, and possibly springing upwards out of the welding die 220.

Figure 19:
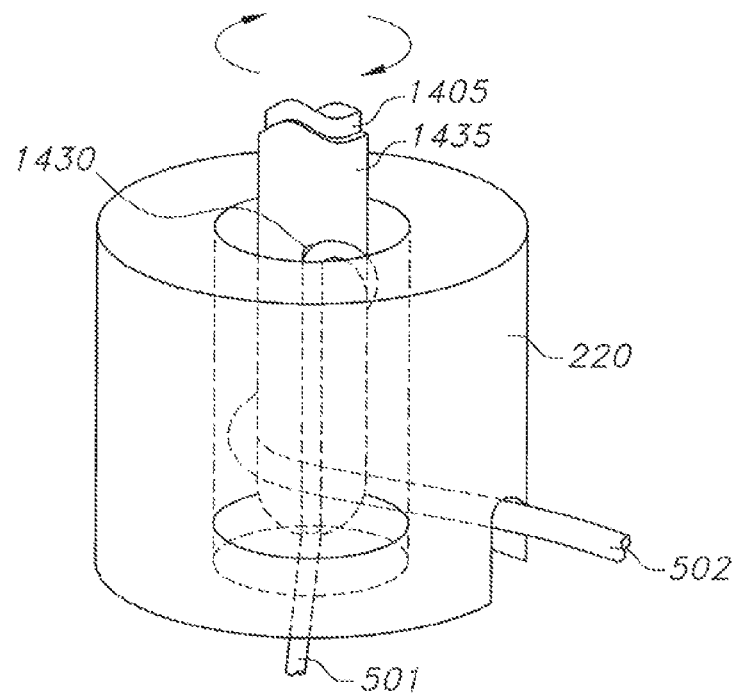
FIG. 19 shows a semi-transparent view of a winding operation of the present invention.

FIG. 19 shows a semi-transparent view of a typical winding operation to indicate the wrapping of the fiber 501 about the winding pin 1400 within the die 220 relative to the passage 1430 of the winding pin 1400. As can be seen, the fiber 501 is wound about the outer surface of the outer cylinder 1435 to form the coiled fiber. Any number of windings may be used to create the coiled fiber (e.g., 801). When the coiled fiber is formed to a desired coil size, the inner cylinder 1405 and outer cylinder 1435 are rotated with respect to each other to create the open passage 1430 extending to the open end 1415 of the pin 1400, in order to facilitate removal of the wound coil (801) from the pin 1400. The coil may be welded, as described above.

Figure 20:
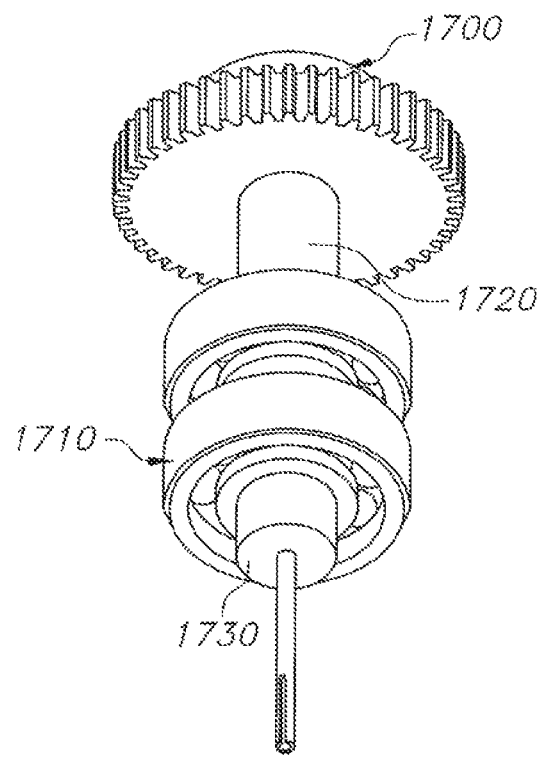
FIG. 20 shows an alternate embodiment of a winding pin drive element.

As seen in FIG. 20, an alternate embodiment of a winding pin drive element is shown. In this embodiment, an engagement element includes a spur gear 1700 mounted to a winding axel 1720, which is in turn coupled to a winding pin base 1730. Additionally, bearings 1710 to support the winding axel 1720 are incorporated to ensure the proper vertical orientation of the winding pin during rotation and to counteract any thrust loading as a result of the winding drive.

Figure 21:
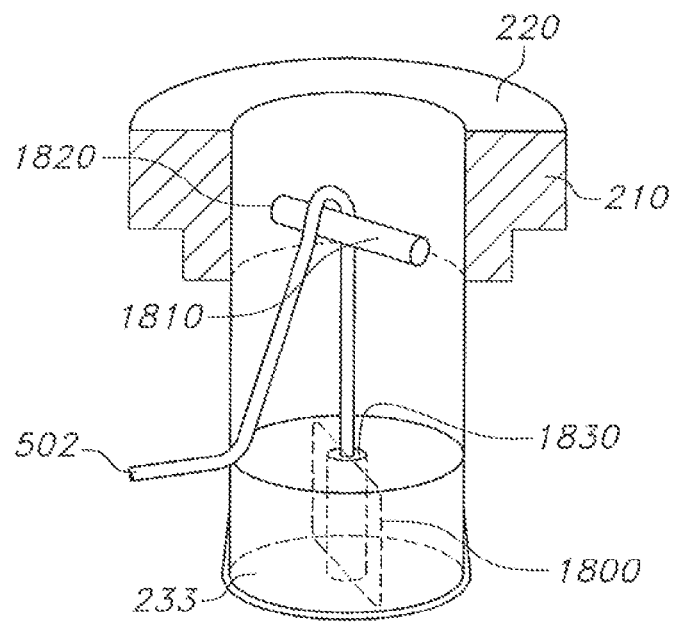
FIG. 21 shows an alternate form of winding a fiber of the present invention using a winding bar.

Referring to FIG. 21, an alternate form of winding is illustrated. In this embodiment, the trailing end of the fiber 502 is threaded through a split welding post 233. The split face 1800 is illustrated. In this variant, the free end of the fiber is passed over a cross member 1810, and is pulled laterally through a channel in the welding die 220. The cross member 1810 may be passed through a bore 1820 in the insert member and is engaged at the opposite end with a pocket located in the opposing side of the through bore of the welding die 220. Additionally, the split face welding post enables full clamping of the fiber 501 during the welding cycle. The clamp surface 1830 of the split post may be produced as a monolithic structure in the base material of the welding post or it may incorporate other compressible or resilient materials to minimize the potential for marring of the compressed fiber. The use of a resilient clamping surface also enables the accommodation of variation in the raw fiber diameter.

Figure 22:
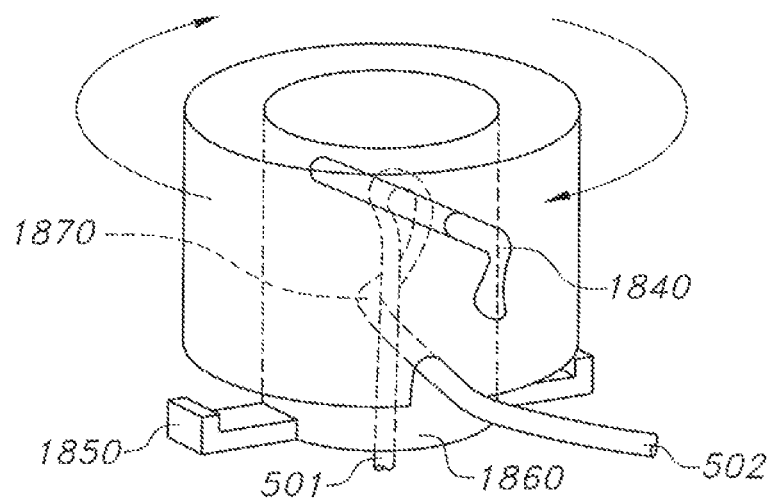
FIG. 22 shows a partially transparent view of the winding operation of FIG. 22.

FIG. 22 shows a partially transparent rendering of the configuration of FIG. 21. The cross member 1810 in this embodiment includes a feature 1840 that is utilized to push or pull the cross member 1810 through the receiving bore. The embodiment incorporates sliding gate like elements 1850 that temporarily maintain the fiber 501 in a clamped or restricted state in the central region of a cylindrical winding pillar 1860. The gate elements 1850 enable the use of winding dies that are more cartridge-like, which may be wound in preparation for welding offline and then inserted into a welding die carrier for welding. Once the cartridge like die is placed upon a split welding post receiver, the split welding post closes up to the final diameter of the desired termination, the gates are opened and the coiled fiber is able to come into contact with the welding post for welding. Unlike the previously described systems, there is no central pin to form the coil during the winding process. Instead, the fiber is wrapped around a clamped vertical fiber element 1870 through the relative rotation of the welding die cartridge about the cylindrical winding pillar. The winding operation may continue until a tightly formed coil is produced, and a slight plastic deformation of the wound fiber occurs. Alternatively, the tightly wound coil may be subjected to a source of thermal energy to enable the stresses within the coil to relieve and for the coil to remain in position.

Figure 23:
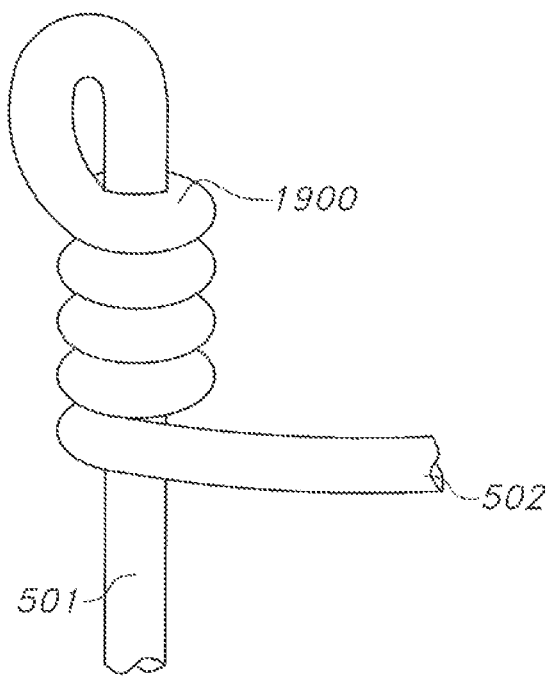
FIG. 23 shows a wound fiber prepared by the operation of FIG. 21.

As seen in FIG. 23, upon completion of the winding operation, the cross member 1810 is released from the winding die, and the resultant coil 1900 is formed.

Figure 24:
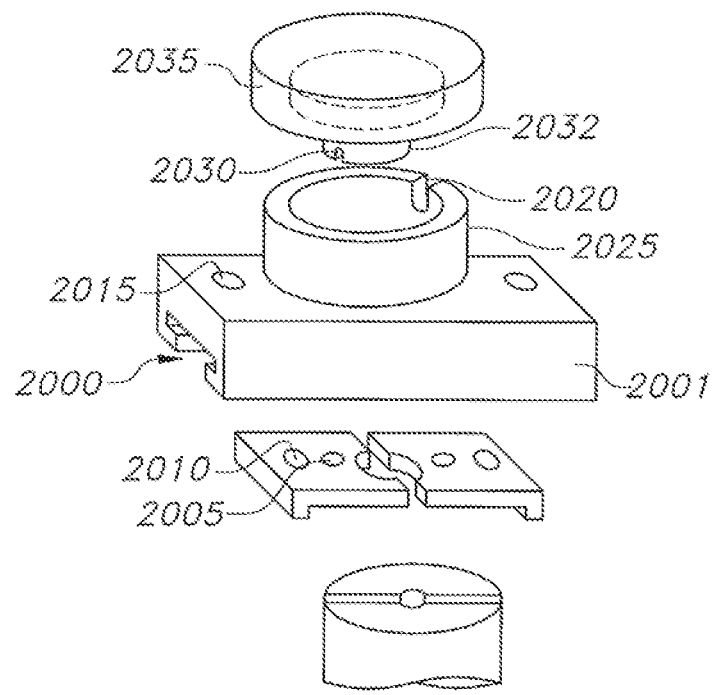
FIG. 24 shows an alternate embodiment of a winding device and welding cartridge of the present invention.

Referring now to FIG. 24, an additional embodiment of a winding device and associated welding cartridge is disclosed. In this embodiment, the winding and welding cartridge utilizes slide gate elements that fit within a receiver track 2000 located on the bottom side of the welding cartridge 2001. Additionally, the gate elements incorporate locator pin holes 2005 and 2010. The outermost locator hole 2010 is utilized during the winding operation to ensure that the fiber (e.g., 501) is guided towards the center of the cartridge during winding. When the cartridge 2001 is placed upon a split welding post for welding, the gates are opened and held in the open position by the inner locator hole 2005. The engagement pin, not shown, that engages the locator holes 2005, 2010 engages with a cartridge locator hole 2015. The first end of the fiber 501 exits from the center bore of the cartridge and the second free end of the fiber 502 passes through a notch 2020 located at the top of the cylindrical portion 2025 of the cartridge 2001. Once the fiber is positioned within the cartridge 2001, a winder knob 2035 is inserted into the upper portion of the cartridge 2001. A notch 2030 located in the winding element 2032 of the knob engages the fiber 501 within the cartridge 2001. The winder knob 2035 is rotated relative to the cartridge 2001. As the knob 2035 is rotated, the first free end of the fiber 501 is maintained in a fixed position and the second free end is drawn into the cartridge 2001 cavity as a coil of fiber is formed about the winder element 2032. Similar to the other embodiments, a stripper 1460 may optionally be included to facilitate removal of the wound coil from the winding element 2032. The winding of fiber in this manner results in the free end of the fiber 502 exiting at the top end of the restraining element and the first end 501 of the fiber bends immediately within the fixture, thus forming into the most proximal coil (803, in FIG. 12) in the coiled fiber.

Figure 25:
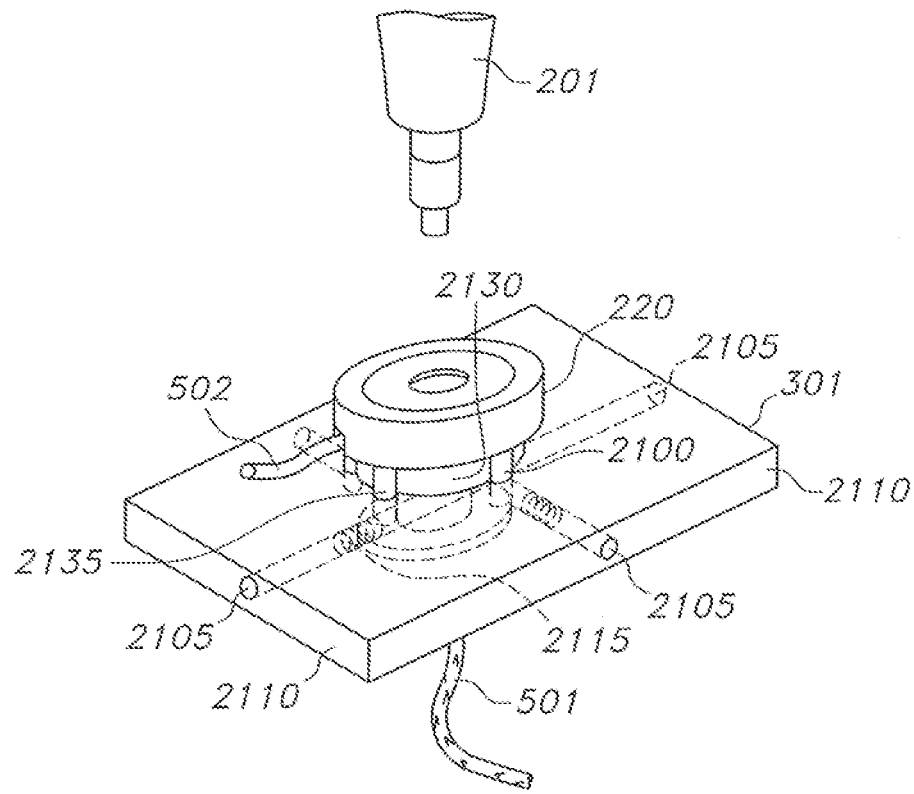
FIG. 25 shows a welding die useful in the present invention.

FIG. 25 shows a welding die 220 as mounted to a series of cage leg elements 2100. The cage leg elements 2100 pass through the mounting plate 301 to the underside assembly of the fixture. The mounting plate 301 has four side edges 2110, which each has at least one threaded passage 2105 therein, wherein each threaded passage 2105 is substantially perpendicular to one of the four edges 2110 of the mounting plate 301. The threaded passages 2105 each independently extend from one edge 2110 towards the center of the mounting plate 301, where each threaded passage 2105 intersects with a through bore passage 2135 intended to receive a cage leg element 2100. Within each threaded passage 2105, at least one ball plunger element 2115 has been installed, where the ball plunger 2115 presses against a cage leg element 2100. Underneath the welding die 220, and above the mounting plate 301, a compressible elastic element 2130 may be provided. It has been found that the quality of the welded terminations is improved through the incorporation of an elastic element 2130, as well as inclusion of the ball plunger elements 2115. The final design may include one or more of the elastic element 2130 or ball plunger elements 2115.

When an elastic element 2130 is placed beneath the welding die 220, it enables the welding die 220 to remain engaged with an ultrasonic welding horn 201 during the application of energy. As the horn 201 oscillates vertically, the spring force acting upon the welding die 220 helps to maintain the welding die 220 in contact during the weld cycle. It has also been found that if the welding die 220 remains in tight engagement with the horn 201 during the welding cycle, the welding of the upper coils of the fiber (e.g. 501) may be diminished and the weld that is produced may be similar in appearance to a weld produced within a cavity in the face of the horn. Preferred welding conditions are achieved through the addition of a frictional drag component to the cage leg elements 2100. The frictional drag component of die movement helps restrict the welding die 220 from vibrating in unison with or in exact frequency with the ultrasonic horn 201 during use. This gives a more uniform welding of the fiber. While the elastic element 2130 and drag elements have been described as being achieved through the use of elastic material and ball plungers, the use of springs, such as air or other types of springs, as well as spiral displacement of the welding die 220, or the use of external damping elements such as brake or shock absorber style elements are also feasible. Thus, in use, it is desired to create a frictional drag of the die movement, which may be achieved through any of the aforementioned means.

What is claimed is:

1. A method of forming a suture comprising the steps of:
   a. winding a second end of a length of suture material, said suture having a first end and second end and a length therebetween, about a winding pin to form a coil, such that the coil does not become entangled, wherein the winding pin includes:
      i. a first cylindrical component having a central axis defining an open interior, the open interior being defined by a side wall and terminating in an open end, the first cylindrical component having a slot extending through the side wall extending from the open end to a termination point axially offset from the open end; and
      ii. a second cylindrical component having a central axis defining an at least partially open interior, the open interior being defined by a side wall and terminating in an open end, the second cylindrical component having a slot extending through the side wall extending from the open end to a termination point axially offset from the open end;
      the first and second cylindrical components being in concentric configuration with each other, wherein the first and second cylindrical components may be independently rotated with respect to each other;
   b. subjecting said coiled second end to application of energy, said energy being sufficient to melt at least a portion of said coiled second end and form a solid unitary termination feature.

2. The method of claim 1, wherein the slot on the first cylindrical component has a first axial configuration and the slot on the second cylindrical component has a second axial configuration, where the first axial configuration is different than the second axial configuration.

3. The method of claim 2, wherein the first axial configuration of the slot on the first cylindrical component includes at least a portion of the slot on the first cylindrical component moves in a substantially straight line parallel to the central axis of the first cylindrical component.

4. The method of claim 3, wherein the second axial configuration of the slot on the second cylindrical component includes the slot on the second cylindrical component being a curvilinear line extending from the open end of the second cylindrical component to the end point on the second cylindrical component.

5. The method of claim 4, wherein when the first cylindrical component and second cylindrical component are in a first configuration, the slot at the open end of the first cylindrical component and the slot at the open end of the second cylindrical component are aligned with each other, creating an open passageway at the open ends of the first and second cylindrical components.

6. The method of claim 4, wherein when the first cylindrical component and second cylindrical component are in a second configuration, the slot at the open end of the first cylindrical component and the slot at the open end of the second cylindrical component are not aligned with each other, thereby creating a closed passageway at the open ends of the first and second cylindrical components and an open passageway between the first and second cylindrical components at a position axially offset from the open ends of the first and second cylindrical components.

7. The method of claim 6, wherein said winding step is caused by rotation of said winding pin while the second end of the suture extends from the open passageway between the first and second cylindrical components at a position axially offset from the open ends of the first and second cylindrical components.

8. The method of claim 1, wherein the coil remains around the outside of the winding pin during said step of forming the termination feature.

9. The method of claim 1, wherein the winding pin is retracted prior to the step of forming the termination feature.

10. The method of claim 1, wherein said termination feature has a cross section selected from the group consisting of circular, rectangular and square shaped.

11. The method of claim 1, wherein the diameter of said termination feature is substantially perpendicular to the central axis of the suture.

12. The method of claim 1, wherein the diameter of said termination feature is substantially parallel to the central axis of the suture.

13. The method of claim 1, wherein the ratio of the diameter of the termination feature to the largest cross-sectional diameter of the suture is from about 1.1:1 to about 10:1.

14. An apparatus for forming a suture having a termination feature comprising:
a. a welding horn having a welding tip;
b. a welding die having an open interior sized to be similar to the welding tip;
c. a winding pin, wherein the winding pin includes:
  i. a first cylindrical component having a central axis defining an open interior, the open interior being defined by a side wall and terminating in an open end, the first cylindrical component having a slot extending through the side wall extending from the open end to a termination point axially offset from the open end; and
  ii. a second cylindrical component having a central axis defining an at least partially open interior, the open interior being defined by a side wall and terminating in an open end, the second cylindrical component having a slot extending through the side wall extending from the open end to a termination point axially offset from the open end;
the first and second cylindrical components being in concentric configuration with each other, wherein the first and second cylindrical components may be independently rotated with respect to each other.

15. The apparatus of claim 14, wherein the slot on the first cylindrical component has a first axial configuration and the slot on the second cylindrical component has a second axial configuration, where the first axial configuration is different than the second axial configuration.

16. The apparatus of claim 15, wherein the first axial configuration of the slot on the first cylindrical component includes at least a portion of the slot on the first cylindrical component moves in a substantially straight line parallel to the central axis of the first cylindrical component.

17. The apparatus of claim 16, wherein the second axial configuration of the slot on the second cylindrical component includes the slot on the second cylindrical component being a curvilinear line extending from the open end of the second cylindrical component to the end point on the second cylindrical component.

18. The apparatus of claim 17, wherein when the first cylindrical component and second cylindrical component are in a first configuration, the slot at the open end of the first cylindrical component and the slot at the open end of the second cylindrical component are aligned with each other, creating an open passageway at the open ends of the first and second cylindrical components.

19. The apparatus of claim 17, wherein when the first cylindrical component and second cylindrical component are in a second configuration, the slot at the open end of the first cylindrical component and the slot at the open end of the second cylindrical component are not aligned with each other, thereby creating a closed passageway at the open ends of the first and second cylindrical components.

20. A method of forming a termination feature on a suture comprising the steps of:
a. placing a distal end of an elongated suture into a welding die, the welding die including an elastic element beneath the welding die;
b. moving at least one of the welding die or a welding horn such that the welding die and welding horn are engaged with each other with the distal end of the elongated suture therebetween;
c. applying energy to the welding horn, such that the welding horn oscillates vertically to deliver energy to the distal end of the elongated suture;
wherein the elastic element provides a spring force to the welding die, allowing the welding die to remain substantially in contact with the welding horn during the application of energy.

21. The method of claim 20, wherein the welding die is capable of vibrating out of synchronization with the welding horn through the use of a dampening element.

* * * * *